(12) United States Patent
Colin et al.

(10) Patent No.: US 6,632,287 B1
(45) Date of Patent: Oct. 14, 2003

(54) METHOD FOR DECONTAMINATING A HOLLOW NEEDLE

(75) Inventors: Bruno Colin, Marcy l'Etoile (FR); Marie Privat, Saint Romain en Gal (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/529,662

(22) PCT Filed: Oct. 27, 1998

(86) PCT No.: PCT/FR98/02561
§ 371 (c)(1),
(2), (4) Date: Apr. 18, 2000

(87) PCT Pub. No.: WO99/27973
PCT Pub. Date: Jun. 10, 1999

(30) Foreign Application Priority Data

Nov. 27, 1997 (FR) .............................. 97 15185

(51) Int. Cl.⁷ ................................ B08B 7/02
(52) U.S. Cl. .................... 134/1; 134/19; 134/22.1; 134/22.18; 134/22.19; 134/25.4; 134/34; 134/35; 110/235; 110/236; 110/250; 110/346
(58) Field of Search ................... 110/235, 236, 110/250, 346; 134/1, 19, 105, 170, 22.1, 22.18, 22.19, 25.4, 34, 35

(56) References Cited

U.S. PATENT DOCUMENTS

| | | |
|---|---|---|
| 3,742,187 A | 6/1973 | Folus |
| 5,375,200 A | 12/1994 | Dugan et al. |
| 5,765,490 A * | 6/1998 | Colin et al. .............. 110/236 |

FOREIGN PATENT DOCUMENTS

| | | |
|---|---|---|
| EP | 0 136 392 A1 | 4/1985 |
| EP | 0 727 228 A1 | 8/1996 |
| FR | 2.091.884 | 1/1971 |
| FR | 2 618 336 | 1/1989 |
| GB | 2 211 420 A | 7/1989 |

OTHER PUBLICATIONS

Academic Press Dictionary of Science and Technology.*

* cited by examiner

Primary Examiner—Randy Gulakowski
Assistant Examiner—M. Kornakov
(74) Attorney, Agent, or Firm—Oliff & Berridge, PLC

(57) ABSTRACT

The invention provides a method and device for decontaminating a contaminated hollow metal needle having electrical wires attached to the needle which heat cleaning fluid dispensed into the needle.

4 Claims, 1 Drawing Sheet

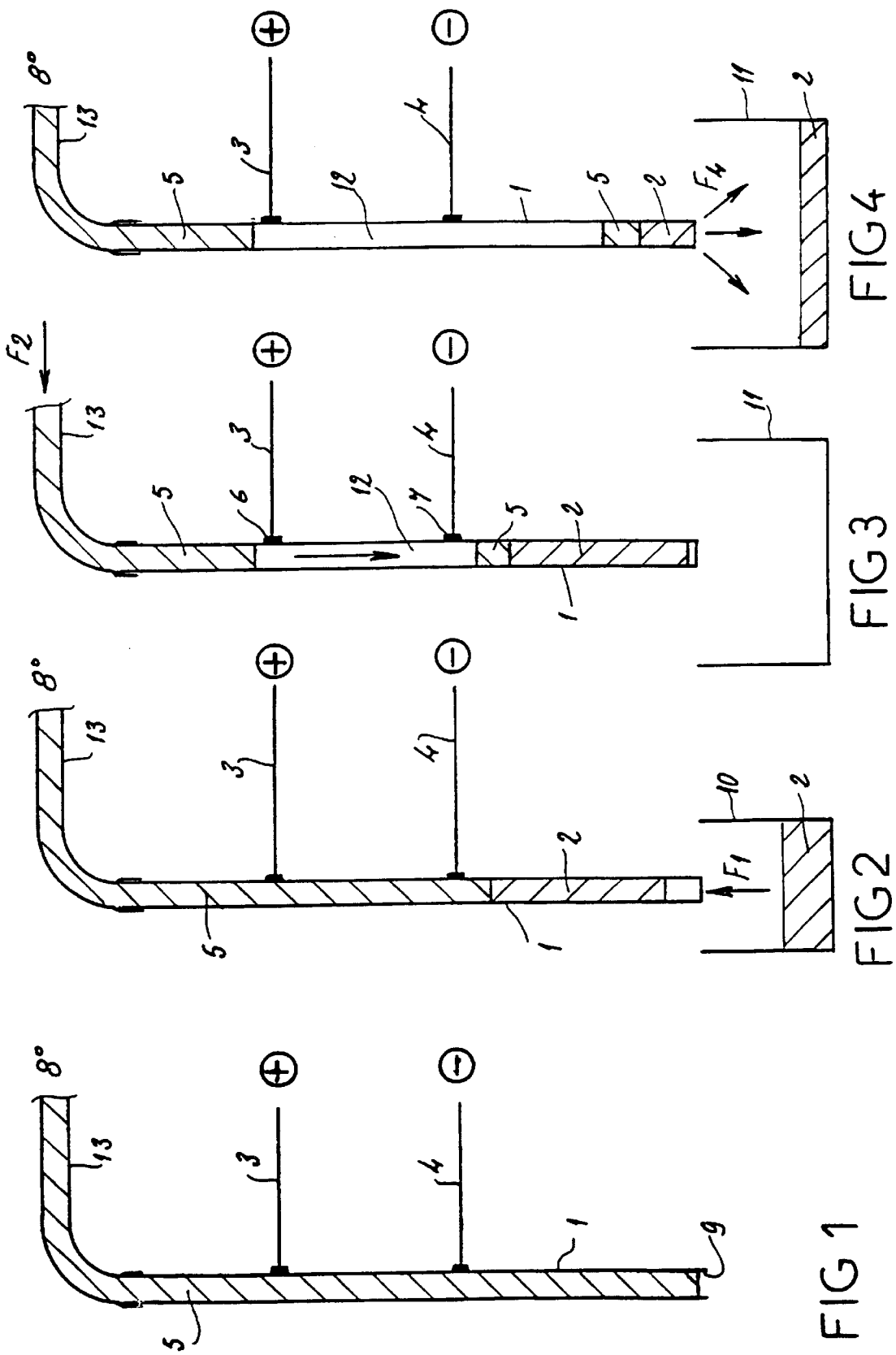

METHOD FOR DECONTAMINATING A HOLLOW NEEDLE

The present invention relates to a method for decontaminating a hollow metal needle intended for sampling and/or dispensing a contaminating liquid, the needle cooperating with electrical wiring means for providing an electric current in the needle for decontaminating and preserving the integrity of the needle with a view to its re-use.

The present invention also relates to a decontamination device which allows the implementation of the above method.

Contaminating liquid is taken to mean any medium which is likely to be processed or manipulated in any method, process or procedure, for example of analysis, but which must be substantially removed or eliminated because, at one time or another it is detrimental to said process, method or procedure, and this being whatever the physical or presentation form of said medium, for example whether it is a material, matter or sample in a liquid or gas or two-phase (liquid + gas) form or alternatively in a powder form, provided that the said medium can be handled as a fluid in particular by aspiration and/or flow reverse.

As a consequence of the previous definition, the terms "contaminated" and "decontaminated" mean, respectively, "bring into contact or introduce a contaminating liquid into or onto an object" and "remove or eliminate the same contaminating liquid from said object".

Ranking highest among the contaminating liquids under consideration by the present invention are biological media, such as samples of fluid or body samplings which can contain or be soiled with various nonpathogenic microorganisms such as viruses, bacteria or other cells. In this case, and for the following description, "contaminating liquid" will mean "non-sterile liquid" and "decontaminated" will mean "sterilized".

However, the present invention is not limited to sterilization, since many other contaminating media can be considered according to the invention. Thus any nucleic acid material or substance, such as DNA, handled in any molecular biology technique can be the subject of the present invention. This is also the case for any organic medium which it is necessary both to handle and to eliminate at one time or another in any process, for example of chemical or biochemical analysis.

However, the common property of all the contaminating liquids considered by the invention is that they can be destroyed by taking the temperature to a relatively high value, for example exceeding 150° C.

The prior art has already proposed methods or devices for efficiently decontaminating hollow metal needles. However, the object of most of the documents of the prior art, such as GB-A-2,211,420, U.S. Pat. No. 5,375,200 or EP-A-0,136,392, is to destroy the needles which have been used.

Such a technique can absolutely not be used with a machine because it considerably increases the cost of using such machines, due to the destruction of very many needles.

Another solution which is particularly evident therefore consists in changing the adapter pieces which are used for the pipettes, it being possible for this technique to be adapted for machines.

In this case, there will be a considerable number of manipulations, which will cause a loss of time on the one hand, and a loss of money on the other.

The latter technique consists in carrying out a washing operation. Most of the current techniques require a large amount of liquid to enable only one hollow needle to be cleaned. On average about 10 ml of cleaning fluid is needed to enable a real decontamination.

However, it has been possible to obtain noticeably better results by other methods, such as that set out in Patent Application EP-A-0,727,228 by the present applicant. It relates to a method for heating a hollow needle consisting essentially of a metal tube whose inside and/or outside have previously been brought into contact with a contaminating medium, according to which an electric current is applied in said needle, which current circulates in the metal wall and depends on the length of said tube, and which resistively dissipates in the latter a heat energy. This method is characterized in that a predetermined amount of electrical energy is supplied in said needle, which is metered as a function of the electrical properties of said tube, on the one hand so as to be enough for the decontamination of the needle both inside and outside, and on the other hand so as to limit the heating and preserve the integrity, including the original shape, of said needle.

The total amount of cleaning fluid is, in this case, considerably less than all the previously described techniques. However, the use of an electrical charge, for example in the needle where the contaminating liquid is present, can cause the crystallization of certain elements of this contaminating liquid, thus harming the quality of the decontamination carried out.

An object of the present invention is therefore to provide a method for decontaminating a hollow needle, but also a device for decontaminating such a hollow needle which requires little cleaning fluid; the method and the device are particularly efficient and economical because they eliminate the contaminated solids (disposable adapter pieces) and reduce the volumes of effluents (contaminated cleaning fluids).

To this end, the present invention relates to a method for decontaminating a hollow metal needle intended for sampling and/or dispensing a contaminating liquid, the needle cooperating with electrical wiring means for providing an electric current in the needle for decontaminating and preserving the integrity of the needle with a view to its re-use, characterized in that it consists:

in injecting a cleaning fluid into the hollow needle having carried out the sampling and/or dispensing of the contaminating liquid, in applying a heat source to all or part of the cleaning fluid present in said hollow needle, and in ejecting said contaminating liquid present and all or part of said cleaning fluid.

According to a first embodiment, the injection of the cleaning fluid and the application of the electrical current are done simultaneously.

According to a second embodiment, the injection of the cleaning fluid takes place prior to the application of the heat source.

According to a third embodiment, the application of the heat source takes place prior to the injection of the cleaning fluid.

The electric current vaporizes all or part of the cleaning fluid present in said hollow needle.

According to one particularly advantageous embodiment, the heat source is due to an electric current.

According to one particularly advantageous embodiment of the method, the ejection is carried out under the action of the pressure of said vaporized cleaning fluid.

The present invention also relates to a device for decontaminating a hollow metal needle intended for sampling and/or dispensing a contaminating liquid, the needle cooperating with electrical wiring means for providing an electric current in the needle for decontaminating and preserving the integrity of the needle with a view to its re-use, characterized in that it comprises at least two electrical wires, each wire connecting a source of electrical energy to the needle; the implementation points of said wires, which form electrodes, are distant from each other, but also from the free end of the needle, and in that the other end of said needle cooperates with a means for dispensing a cleaning fluid.

The contaminating liquid, after the sampling and/or the dispensing, is present between the free end of the hollow needle and the electrode which is closest to said free end.

The cleaning fluid, after the sampling and/or the dispensing, is present between the two electrodes.

According to one particular embodiment, an air bubble is present between the contaminating liquid and the cleaning fluid.

According to another embodiment, the cleaning fluid consists of water.

According to yet another embodiment of the present invention, the cleaning fluid consists of a buffer solution.

The present invention will be described in relation to the attached figures which are not of limiting nature, but represent one particular embodiment of said invention.

The cleaning device according to the invention is associated with a device for external cleaning of the hollow needle.

FIG. 1 represents a schematic view of a hollow needle associated with the decontamination device according to the present invention.

FIG. 2 represents an identical view to FIG. 1, when the contaminating liquid has just been sampled.

FIG. 3 represents an identical view to the above figures, in which the cleaning fluid is vaporized under the action of a discharge of electrical current associated with the injection of additional cleaning fluid.

Finally, FIG. 4 represents an identical view to the above figures, during the ejection of the contaminating liquid and of part of the cleaning fluid.

The present invention relates to a method for decontaminating a hollow needle 1, which is clearly represented in all of FIGS. 1 to 4. This hollow needle 1 is in the approximately vertical position and comprises a free end 9 in the lower position, while its upper end cooperates with a means 8 for dispensing a cleaning fluid 5.

In the figures, only a flexible pipe 13 of the means 8 for dispensing the cleansing fluid 5 is represented, the rest of the dispensing means being symbolically represented by way of the reference numeral 8 in the figures.

Be that as it may, this dispensing means 8 consists essentially of a tank, containing the cleaning fluid 5, which is associated with both a dispensing element, such as a syringe, and a solenoid valve which allows or prevents the functioning of the dispensing element.

The hollow needle 1 is metal and comprises, on its wall, two electrodes 6 and 7 which are connected, via electrical wirings 3 and 4, to an electrical source.

In its position of rest, the device is as represented in FIG. 1, i.e. the hollow needle 1 contains only cleaning fluid 5, this cleaning fluid 5 possibly consisting of water or a buffer solution.

According to FIG. 2, it will be possible, via the dispensing element, to aspirate, according to F1, a specific amount of contaminating liquid 2 contained in a container 10.

When the contaminating liquid 2 is contained in the hollow needle 1, there will be the possibility of releasing it to allow a reaction or a manipulation. Therefore, the needle 1 will be soiled and it will be necessary to decontaminate it.

In the figures, and in order to better visualize the decontamination carried out, the contaminating liquid 2 is not released, and it is the whole of the contaminating liquid 2 which will be the object of the decontamination.

To do this, a potential difference is applied over part of the hollow needle 1, i.e. between the two electrodes 6 and 7. At this level, the cleaning fluid 5 is vaporized 12. Simultaneously, by injection according to F2, cleaning fluid 9 is sent into the hollow needle 1, in such a way that the gas 12 can only be evacuated, because of the increase in volume between the amount of liquid 5, which is going to be vaporized, and the amount of liquid vaporized 12, via the free end 9, under the action F3 of the gas. For this reason, as is represented in FIG. 4, the contaminating liquid 2 is ejected according to F4 into a container 11 provided for this purpose. A part of the cleaning fluid can optionally be combined with this residual contaminating liquid.

For it to be possible to carry this out, the solenoid valve, which allows the cleaning fluid 5 to pass according to F2, is closed just after this injection, such that the cleaning fluid vaporized 12 has to direct the contaminating liquid 2, situated downstream, in the direction of the free end 9 of the hollow needle 1.

During this method, the contaminating liquid 2 must not be present between the two electrodes 6 and 7; for this reason, it is necessary for the electrode situated in the lower position, which is the negative electrode 7, to be sufficiently far away from the free end 9 of the needle 1, so that the contaminating liquid 2 never comes to its level. This being done, the cleaning fluid 5, which will be vaporized 12, enables the ejection, entirely naturally, of the contaminating liquid 2 and thus ensures decontamination of the hollow needle 1.

Since this decontamination is very effective, it will be even more so for smaller amounts of contaminating liquid 2.

Of course, it is possible to combine this internal cleaning of the hollow needle 1 with an already well-known means of external cleaning of the prior art, such as a device for cleaning with the effluents or with a subsidiary liquid.

The fact that the negative electrode 7 is positioned as close as possible to the free end 9 of the needle 1 is not obligatory; this could be the positive electrode 6. Similarly, it is possible for the electric current supplied to be alternating current or direct current.

It is also possible for said electric current to be replaced by any heat source, such as for example a laser, a flame or a plasma torch.

Finally, the simultaneity between the application of the heat source and the injection of the cleaning fluid 5 should be interpreted as corresponding to a time gap of a few tenths of a second to a few hundredths of a second or even a few thousandths of a second. However, it is also possible for the application of the heat source to precede the injection of the liquid 5 and vice versa.

What is claimed is:

1. A method for decontaminating a contaminated hollow metal needle intended for re-use, comprising:

injecting a cleaning fluid into the contaminated hollow needle, in an upstream part of the needle located upstream of an ejection end of the needle with respect to an ejection direction, with any contaminated liquid present in the needle between the ejection end and the cleaning fluid;

applying a heat source to at least one of the contaminated hollow needle and a part of the cleaning fluid present in the hollow needle, so as to vaporize at least part of the cleaning fluid; and ejecting through the ejection end the any contaminated liquid with at least the vaporized part of the cleaning fluid pushing on the any contaminated liquid.

2. The method according to claim 1, wherein the injection of the cleaning fluid and the application of the heat source are done simultaneously.

3. The method according to claim 1, wherein the injection of the cleaning fluid takes place prior to the application of the heat source.

4. The method according to claim 1, wherein the application of the heat source is to the contaminated hollow needle prior to the injection of the cleaning fluid.

* * * * *